United States Patent
Eaton

(10) Patent No.: US 10,111,764 B2
(45) Date of Patent: Oct. 30, 2018

(54) PROSTHESIS INCLUDING RETRACTABLE ANCHORING MEMBERS

(71) Applicant: Cook Medical Technologies LLC, Bloomington, NC (US)

(72) Inventor: Elizabeth A Eaton, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 599 days.

(21) Appl. No.: 14/633,743

(22) Filed: Feb. 27, 2015

(65) Prior Publication Data

US 2015/0245931 A1 Sep. 3, 2015

Related U.S. Application Data

(60) Provisional application No. 61/947,247, filed on Mar. 3, 2014.

(51) Int. Cl.
| | | |
|---|---|---|
| *A61F 2/89* | (2013.01) | |
| *A61F 2/07* | (2013.01) | |
| *A61F 2/848* | (2013.01) | |
| *A61F 2/06* | (2013.01) | |
| *A61F 2/915* | (2013.01) | |

(52) U.S. Cl.
CPC .............. *A61F 2/848* (2013.01); *A61F 2/064* (2013.01); *A61F 2/915* (2013.01); *A61F 2/07* (2013.01); *A61F 2002/8483* (2013.01); *A61F 2002/91575* (2013.01); *A61F 2220/0016* (2013.01); *A61F 2230/0069* (2013.01)

(58) Field of Classification Search
CPC .............. A61F 2/848; A61F 2002/8483; A61F 2002/8486; A61F 2/07; A61F 2/915; A61F 2/064; A61F 2230/0069; A61F 2220/0016

See application file for complete search history.

(56) References Cited

U.S. PATENT DOCUMENTS

| | | |
|---|---|---|
| 5,855,601 A | 1/1999 | Bessler et al. |
| 7,655,037 B2 | 2/2010 | Fleming, III et al. |
| 8,066,755 B2 | 11/2011 | Zacharias et al. |
| 8,083,792 B2 | 12/2011 | Boucher et al. |
| 8,241,346 B2 | 8/2012 | Chobotov |
| 8,252,043 B2 | 8/2012 | Case et al. |
| 8,409,268 B2 | 4/2013 | Swanson et al. |
| 2003/0220683 A1 | 11/2003 | Minasian et al. |
| 2004/0220655 A1 | 11/2004 | Swanson et al. |

(Continued)

*Primary Examiner* — Anh Dang
(74) *Attorney, Agent, or Firm* — Brinks Gilson & Lione

(57) ABSTRACT

A prosthesis may include a tubular frame comprising rings which are concentric along an axis of the tubular frame. The rings may have a serpentine shape with apexes in a longitudinal direction such that the rings are configured to move between a compressed configuration and an expanded configuration. A first ring of the rings can include a first apex that includes a first anchoring member extending radially outward and a first crossbar extending radially inward. The first ring can further include a second apex that neighbors the first apex. The first crossbar can extend toward the second apex and extend radially inward further than the second apex. When in the compressed configuration, the first crossbar can engage the second apex such that the first anchoring member is moved radially inward.

12 Claims, 5 Drawing Sheets

(56) References Cited

U.S. PATENT DOCUMENTS

2009/0082841 A1 3/2009 Zacharias et al.
2010/0274345 A1 10/2010 Rust
2012/0259408 A1 10/2012 Roeder et al.
2014/0277394 A1* 9/2014 Roeder .................. A61F 2/848
   623/1.36

* cited by examiner

PROSTHESIS INCLUDING RETRACTABLE ANCHORING MEMBERS

This application claims the benefit under 35 U.S.C. § 119(e) of U.S. Provisional Application No. 61/947,247, filed Mar. 3, 2014, which is hereby incorporated by reference herein.

BACKGROUND

1. Technical Field

The present invention relates generally to medical prostheses and prosthesis deployment systems for vascular repair. More particularly, the present disclosure relates to a prosthesis and deployment system to repair a transected body vessel for gaining hemostasis during emergency medical procedures.

2. Background Information

Trauma physicians frequently encounter patients having traumatic injury to a body vessel, such as lacerated vessels or even transected vessels, resulting from gunshots, knife wounds, motor vehicle accidents, explosions, etc. Significant damage to a body vessel may expose a patient to deleterious conditions such as the loss of a limb, loss of function of a limb, increased risk of stroke, impairment of neurological functions, and compartment syndrome, among others. Particularly severe cases of vascular injury and blood loss may even result in death. In such severe situations, the immediate goal is to obtain hemostasis while maintaining perfusion of adequate blood flow to critical organs, such as the brain, liver, kidneys, and heart.

Examples of treatment that are commonly performed by trauma physicians to treat body vessel injuries include clamping the vessel with a hemostat, use of a balloon tamponade, ligation of the damaged vessel at or near the site of injury, or the insertion of one or more temporary shunts. However, conventional surgical repair is generally difficult with such actively bleeding, moribund patients. In many instances, there is simply not enough time to repair the body vessel adequately by re-approximating and suturing the body vessel. In many situations, the trauma physician will simply insert a temporary shunt (such as a Pruitt-Inahara Shunt) into the vessel. However, use of temporary shunts has been linked to the formation of clots. This may require returning the patient to the operating room for treatment and removal of the clots, often within about 36 to 48 hours of the original repair. Since shunts are generally placed as a temporary measure to restore blood flow and stop excessive blood loss, the shunt is typically removed when the patient has stabilized (generally a few days later) by a specialized vascular surgeon. After removal, the vascular surgeon will replace the shunt with a vascular graft, such as a fabric graft that is sewn into place. Ligation of the damaged blood vessel may result in muscle necrosis, loss of muscle function, or a potential limb loss or death.

Due to the nature of the body vessel injury that may be encountered, the use of shunts, repairing and/or ligating of a blood vessel often requires that such treatments be rapidly performed at great speed, and with a high degree of physician skill. Such treatments may occupy an undue amount of time and attention of the trauma physician at a time when other pressing issues regarding the patient's treatment require immediate attention. In addition, since the level of particularized skill required may exceed that possessed by the typical trauma physician, particularly traumatic episodes may require the skills of a physician specially trained to address the particular trauma, such as a vascular trauma, and to stabilize the patient in the best manner possible under the circumstances of the case.

Some open surgical techniques utilize sutures to affix damaged tissue portions surrounding fittings that have been deployed with the vessel, which requires the trauma physician to take time to tie the sutures properly. Although in modern medicine sutures can be tied in relatively rapid fashion, any step in a repair process that occupies physician time in an emergency situation is potentially problematic. In addition, the use of sutures to affix the vessel to the fitting compresses the tissue of the vessel against the fitting. Compression of tissue may increase the risk of necrosis of the portion of the vessel tissue on the side of the suture remote from the blood supply. When present, necrosis of this portion of the vessel tissue may result in the tissue separating at the point of the sutures. In this event, the connection between the vessel and the fitting may eventually become weakened and subject to failure. If the connection fails, the device may disengage from the vessel. Therefore, efforts continue to develop techniques that reduce the physician time required for such techniques, so that this time can be spent on other potentially life-saving measures.

It would be desirable to provide a prosthesis deployment system for use in open surgical repair of an injured body vessel, such as an artery or a vein, (and in particular a transected vessel) during emergency surgery in a manner that is time effective, that addresses the trauma at hand to the extent possible, and that utilizes techniques that may be readily practiced by an trauma physician.

SUMMARY

The problems of the prior art are addressed by the prosthesis of the present invention. In one form thereof, a prosthesis for engaging with a body vessel includes a tubular frame comprising rings which are concentric along an axis of the tubular frame. The rings may have a serpentine shape with apexes in a longitudinal direction such that the rings are configured to move between a compressed configuration and an expanded configuration. A first ring of the rings can include a first apex that includes a first anchoring member extending radially outward and a first crossbar extending radially inward. The first ring can further include a second apex that neighbors the first apex. The first crossbar can extend toward the second apex and extend radially inward further than the second apex. When in the compressed configuration, the first crossbar can engage the second apex such that the first anchoring member is moved radially inward.

In another form thereof, a method of engaging a prosthesis with a body vessel includes providing a tubular frame in a compressed configuration within a sheath. The tubular frame can include rings which are concentric along an axis of the tubular frame. The rings can have a serpentine shape with apexes in a longitudinal direction such that the rings are configured to move between the compressed configuration and an expanded configuration. A first ring of the rings can include a first apex that includes a first anchoring member extending radially outward and a first crossbar extending radially inward. The first ring can further include a second apex that neighbors the first apex. The first crossbar can extend toward the second apex and extend radially inward further than the second apex. When in the compressed configuration, the first crossbar can be engaged with the second apex such that the first anchoring member is radially inward further than the second apex. The method can further include inserting the tubular frame into the body vessel, removing the sheath from the tubular frame, and expanding the tubular frame to the expanded configuration thereby disengaging the crossbar from the second apex so that the anchoring member extends radially outward further than the second apex to engage with the body vessel.

In a further form thereof, a method of interconnecting a first vessel portion and a second vessel portion of a transected body vessel includes forming an opening in the first vessel portion spaced from a first end of the first vessel portion. The method can further include inserting a prosthesis delivery system through the opening. The prosthesis delivery system can include a sheath having a passageway, an inner catheter disposed within the passageway of the sheath, and a prosthesis disposed between the sheath and the inner catheter. The prosthesis can be in a compressed configuration within the sheath. The prosthesis can include anchoring members that are retracted while the prosthesis is in the compressed configuration such that the anchoring members are disengaged with the sheath. The method can further include retracting the sheath relative to the inner catheter to deploy the prosthesis in an expanded configuration. The anchoring members can extend radially outward when the prosthesis is in the expanded configuration such that one of the anchoring members engages with the first vessel portion and another of the anchoring members engages with the second vessel portion.

BRIEF DESCRIPTION OF THE DRAWINGS

The invention may be more fully understood by reading the following description in conjunction with the drawings, in which.

DETAILED DESCRIPTION

Figure 1:
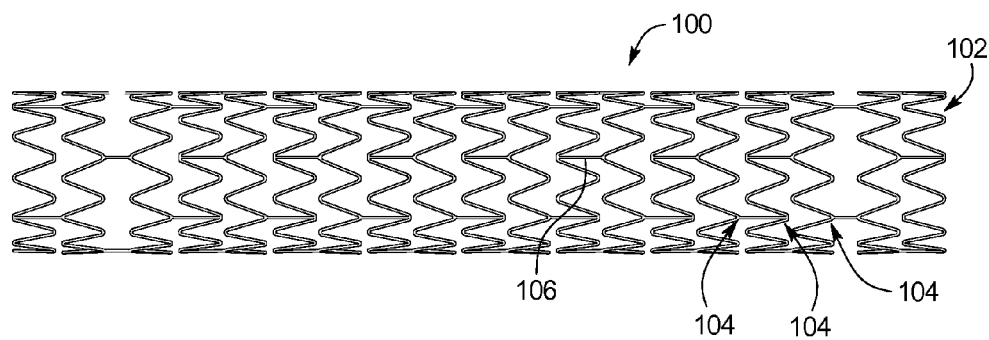
FIG. 1 is a side view of a prosthesis according to an embodiment of the present application.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The prosthesis delivery systems described herein can be useful for open surgical repair of a body vessel, such as a blood vessel, during a medical procedure such as an emergency open surgical procedure. The prosthesis deployment systems can be particularly useful to deliver a prosthesis for repair of a lacerated artery or vein during emergency surgery, and particularly, to obtain hemostasis while maintaining blood perfusion, especially after transection of the body vessel.

Figure 2:
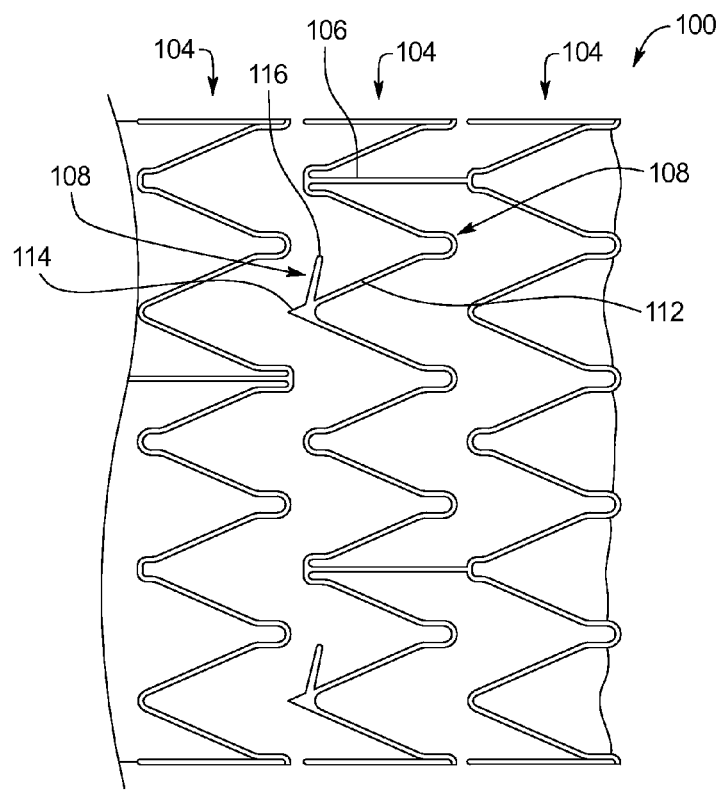
FIG. 2 is an enlarged view of an end portion of the prosthesis of FIG. 1.

FIG. 1 is a side view of an example of a prosthesis 100. The prosthesis 100 can be part of a prosthesis delivery system to implant the prosthesis 100 into a patient. The prosthesis 100 can include a tubular frame 102 that includes a plurality of rings 104 which are concentric along an axis of the tubular frame 102 in a longitudinal direction. The rings 104 can each be coupled to a neighboring ring 104 such as with a cross support 106. FIG. 2 is an enlarged view of an end of the prosthesis 100. The rings 104 can have a serpentine shape that includes apexes 108 in the longitudinal direction such that the ring 104 can bend in a region of the apexes 108 to move between a radially compressed configuration and a radially expended configuration. Struts 112 can extend between adjoining apexes 108 to form the ring 104.

One or more of the apexes 108, 110 can include an anchoring member 114 such as a barb that extends radially outward. Furthermore, the anchoring member 114 may also extend longitudinally. For example, the anchoring member 114 may extend longitudinally toward a center of the tubular frame 102 (as shown in FIG. 2), or the anchoring member 114 may extend longitudinally toward an end of the tubular frame 102. When the prosthesis 100 is implanted in a body vessel, the anchoring member 114 can engage with the vessel to restrict longitudinal movement of the prosthesis 100 within the vessel. A sheath can be used to retain the prosthesis 100 in the compressed configuration until the prosthesis 100 is delivered to a target site in the vessel. The sheath can be slid off of the prosthesis 100 to deploy the prosthesis 100. However, certain anchoring members may engage with the sheath and prevent deployment of a prosthesis. The prostheses 100 described herein can be configured to retract radially inward the anchoring members 114 while in the compressed configuration, and configured to extend radially outward the anchoring members 114 while in the expended configuration. Thus, the prosthesis 100 described herein may not engage with a sheath that retains the prosthesis 100 in the compressed configuration.

Figure 3A:
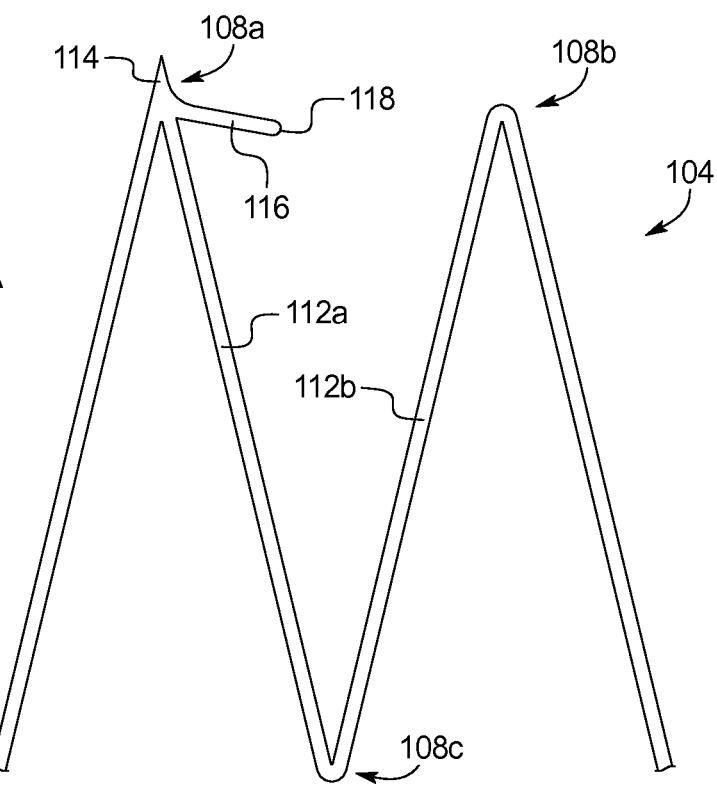
FIG. 3A is a section of a ring of the prosthesis of FIG. 2 with an apex having an anchoring member and crossbar in an expanded configuration.
Figure 3B:
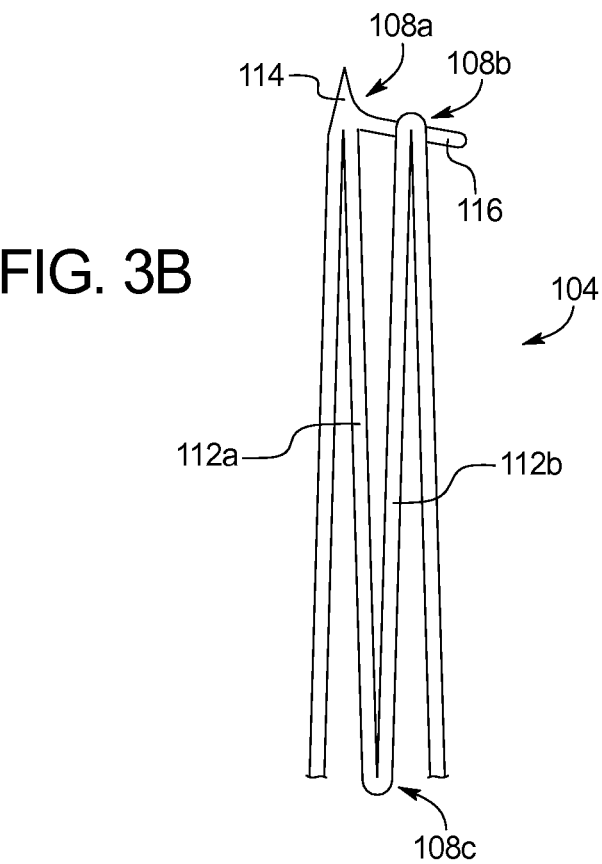
FIG. 3B is the prosthesis of FIG. 3A in a compressed configuration.

FIGS. 3A and 3B depict a top view of a portion of a ring 104 showing three apexes 108a, 108b, 108c in the expanded configuration and the compressed configuration, respectively. A first apex 108a includes an anchoring member 114 that extends radially outward. For example, the first apex 108a can extend radially outward further than a second apex 108b. The second apex 108b and the third apex 108c can be generally flush with an outer surface of the prosthesis 100. The first apex 108a and the second apex 108c can extend in a first longitudinal direction and the third apex 108c can extend in a second longitudinal direction. For example, the apexes 108a, 108b, 108c can be bends in the ring 104 to form the serpentine shape. A first strut 112a can extend between the first apex 108a and the third apex 108c, and a second strut 112b can extend between the second apex 108b and the third apex 108c.

When the ring 104 is compressed, distance between neighboring apexes such as a distance between the first apex 108a and the second apex 108b decreases. The first apex 108a can include a crossbar 116 extending toward a neighboring apex such as the second apex 108b. The crossbar 116 can extend from the first apex 108a, extend from a position adjacent to the first apex 108, or a position along the first strut 112a spaced from the first apex 108a. The crossbar 116 can also extend radially inward in a tapering manner. In particular, a distal end 118 of the crossbar 116 can extend radially inward beyond the second apex 108b. Thus, as the first apex 108a and the second apex 108b move toward one another, the distal end 118 of the crossbar 116 can pass under (e.g., radially inward) the second apex 108b. As the first apex 108a and the second apex 108b continue to move closer to one another, the crossbar 116 can engage with the second apex 108b. For example, the second apex 108b may have a notch or ramp on a luminal surface that engages with the crossbar 116. Since the crossbar 116 is angled radially inward from the first apex 108a to the distal end 118, the second apex 108b can slide along the crossbar 116. Thus, as the first apex 108a and the second apex 108b continue to move closer to one another, the first apex 108a and the second apex 108b can move radially away from one another.

Figure 4A:
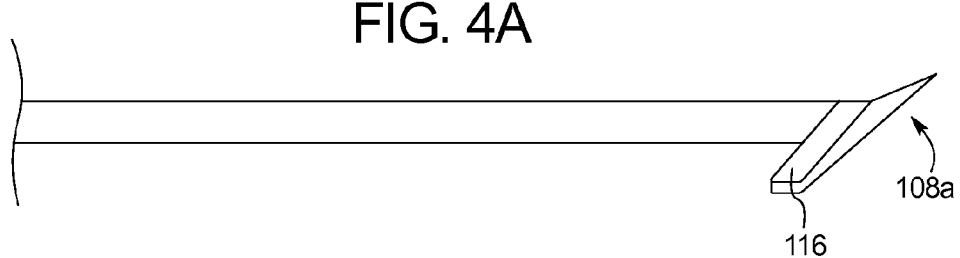
FIG. 4A is a side plane view of a section of a ring of a prosthesis showing an apex that includes an anchoring member and a crossbar according to an embodiment of the present application.
Figure 4B:
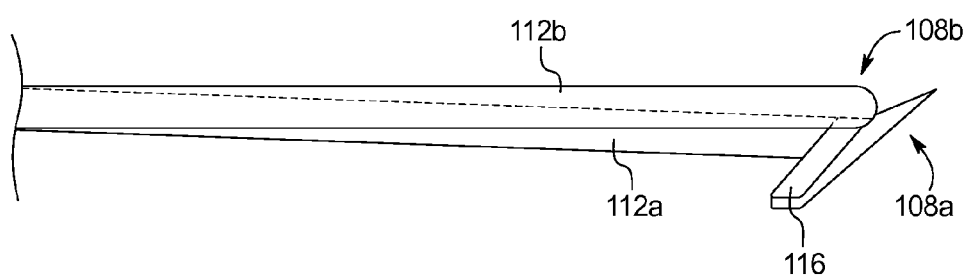
FIG. 4B includes the apex of FIG. 4A and a neighboring apex engaged with the crossbar in a compressed configuration.

FIG. 4A is a side plane view of another example of a first apex 108a with a crossbar 116, and FIG. 4B is a side plane view of a crossbar 116 engaging with a second apex 108b. The second apex 108b is shown as being in front of the first apex 108a. As the first apex 108a and the second apex 108b move even closer to one another, the engagement of the crossbar 116 and the second apex 108b can cause the first apex 108a and the second apex 108b to move radially away from one another. For instance, the first apex 108a can move radially inward and/or the second apex 108b can move radially outward. Thus, in the compressed configuration, the anchoring member 114 can be radially inward further than the second apex 108b, which can prevent or reduce engagement of the anchoring member 114 with a sheath that maintains the prosthesis 100 in the compressed configuration.

The prosthesis 100 may be configured so that apexes 108 without an anchoring member 114 such as the second apex 108b do not substantially radially extend outward when in the compressed configuration. For example, even though the apexes 108 with an anchoring member 114 do not have an anchoring member 114 that can engage with a sheath, if the apex 108 extends beyond the outer surface of the prosthesis 100, the apex 108 may inhibit removal of the sheath from the prosthesis 100. For example, the first apex 108a and/or the first strut 112a may deform while the second apex 108b and the second strut 112b do not substantially deform. For instance, the first apex 108a and/or the first strut 112a may have a cross-sectional area smaller than a cross-sectional area of the second apex 108b and the second strut 112b. In particular, the anchoring member 108a can have a sharp point such a barb which can bend radially inward since the sharp point can have a cross-sectional area less than a cross-sectional area of other components of the ring 104. In another example, a cross support 106 may be coupled to the second apex 108b, which may increase rigidity of the second apex 108b.

Figure 5:
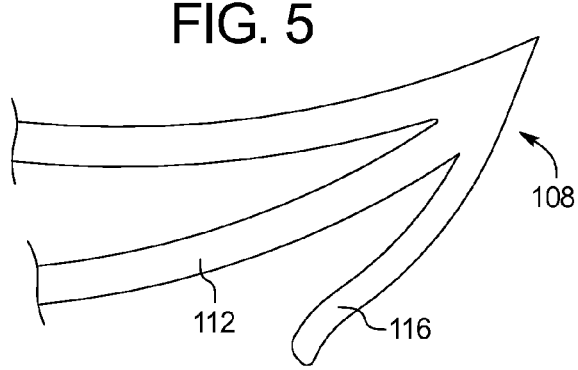
FIG. 5 is a perspective view of a peak with an anchoring member and crossbar extending from the anchoring member according to an embodiment of the present application.

FIG. 5 is another example of an apex 108 with an anchoring member 114 and a crossbar 116 extending from the anchoring member 114. The crossbar 116 extends away from the anchoring member 114 toward a neighboring apex and radially inward, as described above. The crossbar 116 can also extend in a direction of the strut 112. For example, the neighboring apex may also include an anchoring member. Thus, the crossbar 116 can extend toward a non-radially outward extended portion of the neighboring apex. As described above, the anchoring member 114 can be configured to bend while the strut 112 may not substantially bend in the compressed configuration. Therefore, neighboring apexes may both have an anchoring member 114 and may be moved radially inward when in the compressed configuration.

Figure 6:
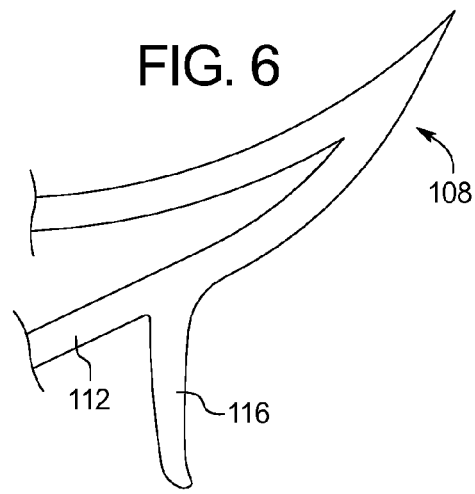
FIG. 6 is a perspective view of a peak with an anchoring member and crossbar spaced from the anchoring member according to an embodiment of the present application.

FIG. 6 is a further example of an apex 108 with an anchoring member 114 and a crossbar 116 spaced from the anchoring member 114. The crossbar 116 may extend from the strut 112. Thus, the crossbar 116 may engage with a strut of a neighboring apex when in the compressed configuration. Furthermore, the crossbar 116 may not extend in a direction of the strut 112. For example, if the neighboring apex does not include an anchoring member, the crossbar 116 may not necessarily be angled to avoid an anchoring member of the neighboring apex. Thus, the crossbar 116 may extend from the apex 108 in a generally perpendicular direction.

Figure 7:
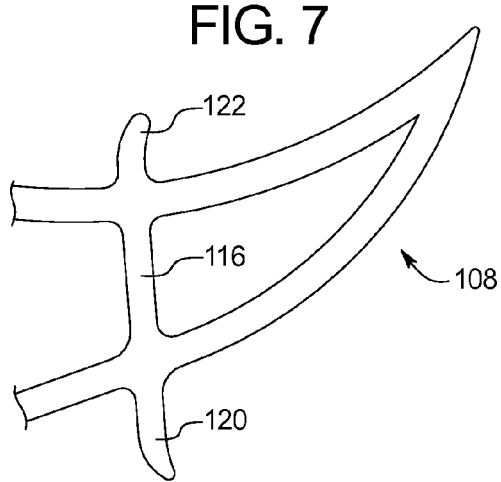
FIG. 7 is a perspective view of a peak with an anchoring member and crossbar extending in two directions according to an embodiment of the present application.

FIG. 7 is an even further example of an apex 108 with a crossbar 116 extending toward both neighboring apexes. The crossbar 116 can extend across both struts 112 that extend from the apex 108, or the crossbar 116 may not extend between the struts 12. For example, a first portion 120 of the crossbar 116 may extend toward a first neighboring apex, and a second portion 122 of the cross bar 116 may extend toward a second neighboring apex. As such, in the compressed configuration, the first portion 120 may engage the first neighboring apex and the second portion 122 may engage with the second neighboring apex to move the apex 108 radially inward.

Figure 8A:
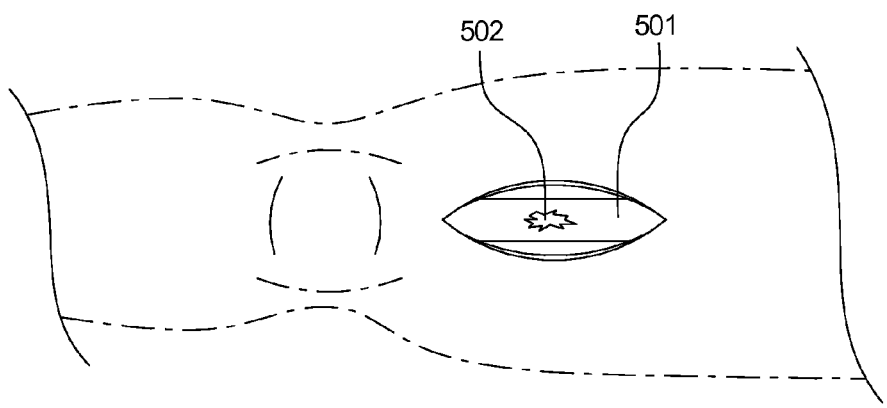
FIG. 8A is a perspective view of a damaged portion of a body.
Figure 8B:
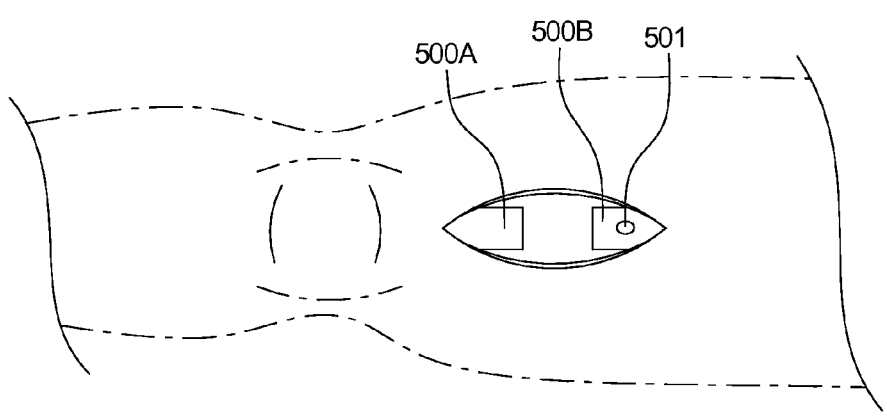
FIG. 8B is a perspective view of the body vessel of FIG. 8A with the damaged portion transected and an opening formed in a healthy portion of the vessel that is adjacent to the transected portion.

Although the described prosthesis with the anchoring member may be configured to be used in a variety of medical procedures, repair of vascular trauma is described herein in relating to a prosthesis delivery system for implanting the prosthesis. FIGS. 8A-8D illustrate a method of delivering a prosthesis to a transected body vessel to interconnect the two vessel portions during open surgery. In FIG. 8A, a body vessel 500, for example in the leg of a patient, has previously been subjected to a traumatic episode, which results in a portion 502 of body vessel 500 being torn away or otherwise severely damaged. Pre-surgery preparation may be applied to the leg and a trauma pathway may be formed therein in order to gain access to the body vessel and the damaged portion thereof. The body vessel 500 on both ends of the damaged portion 502 may be clampled to restrict blood flow temporarily. The blood vessel 500 can be cut or transected if necessary or desired into two portions 500A, 500B by the clinician, as shown in FIG. 8B. The transection may be at the damaged portion 502 of the vessel 500 or as far away as necessary from the damaged portion to remove unhealthy portions of the body vessel or unrepairable portions of the body vessel 500. Sutures can, for example, be attached to the end openings 505 of body vessel portions 500A, 500B to keep them fixed in place and opened to facilitate insertion of the prosthesis 100. Forceps may also be used in a similar manner. Alternatively, the vessel 500 may not be cut or transected; however, the vessel 500 may still have vessel portions 500A, 500B on either side of the damaged portion 502. Thus, the vessel 500 may be left as-is. A prosthesis 100 can be selected to have a radial expanded cross-section and a longitudinal length sufficient to bridge the body vessel portions 500A, 500B and to radially fit within the body vessel portions 500A, 500B.

In order for the prosthesis delivery system to be inserted into the vessel 500, an opening 501 can be formed in a relatively healthy portion of the body vessel 500 away from the damaged portion 502 of the vessel 500. The opening 501 may be an incision or a puncture formed by surgical methods such as with a scalpel or a needle. For example, the opening 501 can be formed by inserting a needle into the vessel 500, and a dilator and/or sheath can be used to maintain a channel through the vessel 500 so that the prosthesis delivery system can be inserted through the opening 501 and into the interior of the vessel 500.

Figure 8C:
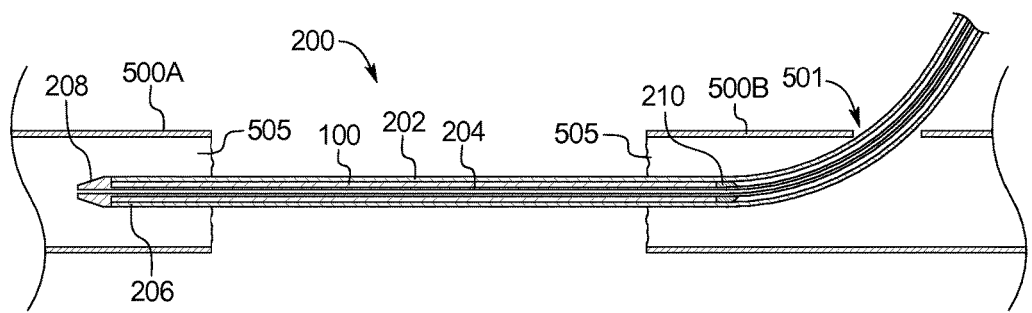
FIG. 8C is a cross-sectional side view of a prosthesis delivery system according to an embodiment of the present application inserted through a healthy portion of vessel and extends between portions of the vessel.

As depicted in FIG. 8C, the prosthesis delivery system 200 has been inserted through the opening 501 and positioned at the target site to deploy the prosthesis 100 between the body vessel portions 500A, 500B. The delivery system 200 can include a sheath 202 to retain the prosthesis 100 in the compressed configuration. The sheath 202 can have a passage extending from a distal end to a proximal end.

The delivery system 200 can also include an inner catheter 204 that can be within the passage of the sheath 202. Furthermore, the inner catheter 204 can extend through the prosthesis 100 such that prosthesis 100 is positioned between the sheath 202 and the inner catheter 204. The inner catheter 204 can also have a passage extending from a distal end to a proximal end. A guide wire can be used to reach a target site within a patient that the medical device is to be deployed. The delivery system 100 can then be slid over the guide wire such that the guide wire extends though the passage of the inner catheter 204.

The distal end 208 of the inner catheter 204 can extend longitudinally beyond the distal end 206 of the sheath. The distal end 208 of the inner catheter 204 can extend radially outward to the sheath 202 to restrict longitudinal movement of the prosthesis 100 in a distal direction. The inner catheter 204 can further include a pusher band 210 adjacent to a proximal end of the prosthesis 100 to restrict longitudinal movement of the prosthesis 100 in a proximal direction.

Figure 8D:
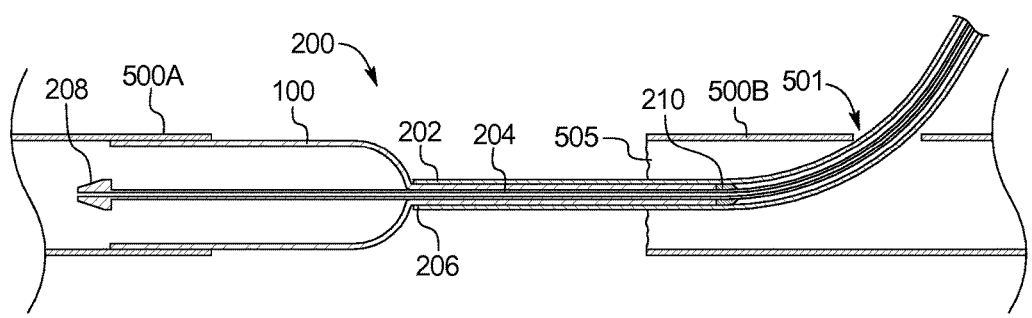
FIG. 8D is a cross-sectional side view of the prosthesis delivery system of FIG. 8B showing partial deployment of a prosthesis.

To deploy the prosthesis 100, the sheath 202 can be moved proximally relative to the inner catheter 204, as depicted in FIG. 8D. The prosthesis 100 can be self-expanding so that as the sheath 202 is removed, the prosthesis 100 can expand against the walls of the vessel 500. As described above, the prosthesis 100 can be configured to have the anchoring members pulled radially inward while in the compressed configuration in the deployment system 200. Thus, the sheath 202 can slide off of the prosthesis 100 without the anchoring members engaging with the sheath 202. When the prosthesis 100 is in an expanded configuration, the anchoring members can radially protrude outward from prosthesis 100 and engage with walls of the vessel 500.

Figure 8E:
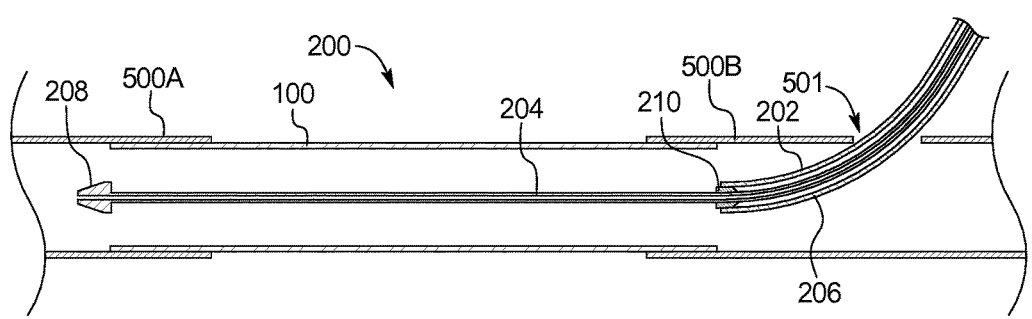
FIG. 8E is a cross-sectional side view of the prosthesis delivery system of FIG. 8C showing complete deployment of the prosthesis.

FIG. 8E depicts the prosthesis 100 completely deployed and implanted in the patient. The prosthesis 100 extends between the first vessel portion 500A to the second vessel portion 500B to provide a continuous lumen between the first vessel portion 500A and the second vessel portion 500B. Thus, the prosthesis 100 interconnects the first and second portions 500A, 500B of the transected body vessel to form a passageway for blood flow. The sutures, if present, can then be removed. Preferably, portions of the exterior surfaces of the prosthesis sealably engage with the luminal walls of the body vessel to inhibit leakage of blood and to force blood to flow throughout the body vessel during emergency surgery, and particularly to obtain hemostasis while maintaining blood perfusion. The prosthesis 100 can be permanently placed within the patient, thereby obviating a need for subsequent surgical intervention.

Although the prosthesis and the deployment system has been described in connection with its primary intended use for repair of vascular trauma, those skilled in the art will appreciate that the prosthesis and the deployment system may also be used to repair other traumatic conditions. Non-limiting examples of such conditions include aneurysms, such as abdominal aorta aneurysms, and surgery for tumor removal. In another matter of terminology there are many types of body canals, blood vessels, ducts, tubes, and other body passages, and the term "body vessel" is meant to include all such passages. Other vascular applications include coronary arteries, carotid arteries, vascular aneurysms, and peripheral arteries and veins (e.g., renal, iliac, femoral, popliteal, subclavian, aorta, intracranial, etc.). Other nonvascular applications include gastrointestinal, duodenum, biliary ducts, esophagus, urethra, reproductive tracts, trachea, and respiratory (e.g., bronchial) ducts. To this end, the deployment systems and methods described herein can be used to deliver a prosthesis to any of these vessels, ducts, canals, tubes or body passageways.

Furthermore, the prosthesis with retractable anchoring members has been described in connection with prostheses for repair of vascular trauma. However, those skilled in the art will appreciate that the retractable anchoring members can be used with other prostheses for other medical procedures. For example, the retractable anchoring members can be included in various other stent configurations that may be deployed from a sheath.

The prosthesis 100 can be any type of implant, stent, graft or conduit that is used for medical applications, and an exemplary prosthesis is shown in the figures. The prosthesis can include a generally tubular graft portion and one or more stent structures that are attached to the graft. The prosthesis can be expandable between the radially compressed, delivery configuration that is shown in FIG. 1, to the radially expanded, deployed configuration. The stent structure can be attached to an outer surface of the graft so that a lumen of the graft may provide a clear path for fluid flow, and/or attached to the inner surface of the graft. The prosthesis can be sized and shaped for suitable placement within a body vessel, such as an artery or vein, and most particularly, for placement at the site of a vascular trauma such as a transected vessel. The stent structure can be any pattern of stent structures in the art and can be self-expanding or balloon expandable.

The anchoring member can inhibit migration of the prosthesis after deployment or detachment of the vessel wall from the prosthesis. The anchoring member can include barbs or various shaped member structures, including fibers, bristles, or outer protruding and penetrable media.

The graft can be a liner that extends at least entirely along the luminal wall, abluminal wall, or both the luminal and abluminal walls of the stent structure. The graft can be made of material to inhibit fluid or blood located within the prosthesis lumen from passing through the graft. In other words, fluid flow is urged by the graft to enter into one end and exit out of the other end of the prosthesis. The graft can be formed from conventional materials well known in the medical arts. It is preferred that the graft covering have a porosity (e.g., about 10 to about 150 μm) for sufficient capillarization and be relatively thin as possible (e.g., about 0.005 inches to about 0.010 inches, and preferably about 0.001 to about 0.0035 inches). Examples of pore density and pore size for the graft covering, as well as other types of materials for a graft covering can be found in U.S. Pat. No. 7,244,444 to Bates, which is incorporated herein by reference in its entirety. A particularly preferred material is expanded polytetrafluoroethylene (ePTFE). Other materials that may be suitable in a particular case include, among others, polytetrafluoroethylene, silicone, polyurethane, polyamide (nylon), as well as other flexible biocompatible materials. Graft covering can also be formed from known fabric graft materials such as woven polyester (e.g. DACRON®), or from a bioremodelable material. One exemplary graft material is THORALON® from Thoratec Corporation (Pleasanton, Calif.), that can prevent leakage of fluid through the pores of the graft. THORALON® is a polyetherurethane urea blended with a siloxane containing surface modifying additive, and has been demonstrated to provide effective sealing of textile grafts. Another example is polyethylene, and in particular, an ultra-high molecular weight polyethylene (UHMwPE), commercially available as DYNEEMA®. The graft may also include a bioremodelable material that can provide an extracellular matrix that permits, and may even promote, cellular invasion and ingrowth into the material upon implantation. Non-limiting examples of suitable bioremodelable materials include reconstituted or naturally-derived collagenous materials. Suitable collagenous materials may include an extracellular matrix material (ECM) that possesses biotropic properties, such as submucosa, renal capsule membrane, dermal collagen, dura mater, pericardium, fascia lata, serosa, peritoneum or basement membrane layers. Suitable submucosa materials may include, for example, intestinal submucosa, including small intestinal submucosa (SIS), stomach submucosa, urinary bladder submucosa, and uterine submucosa. One non-limiting example of a suitable remodelable material is the SURGISIS® BIODESIGN™, which is commercially available from Cook Medical Inc. (Bloomington, Ind.). Another suitable remodelable material is the graft prosthesis material described in U.S. Pat. No. 6,206,931 to Cook et al., incorporated herein by reference. The remodelable material can be ECM, SIS, remodelable or collagenous foam, foamed ECM, lyophilized SIS, vacuum pressed SIS, or the like.

The prosthesis can also include a coating of one or more therapeutic agents along a portion of the conduit body and/or the graft coverings. Therapeutic agents for use as biocompatible coatings are well known in the art. Non-limiting examples of suitable bio-active agents that may be applied to the vascular conduit include thrombo-resistant agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Those skilled in the art will appreciate that other bioactive agents may be applied for a particular use. The bioactive agent can be incorporated into, or otherwise applied to, portions of the vascular conduit by any suitable method that permits adequate retention of the agent material and the effectiveness thereof for its intended purpose.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A prosthesis for engaging with a body vessel comprising:
    a tubular frame comprising rings which are concentric along an axis of the tubular frame, the rings have a serpentine shape with apexes in a longitudinal direction such that the rings are configured to move between a compressed configuration and an expanded configuration, a first ring of the rings comprises:
    a first apex comprising:
        a first anchoring member extending radially outward; and
        a first crossbar extending radially inward; and
    a second apex that neighbors the first apex,
    wherein the first crossbar extends toward the second apex and extends radially inward further than the second apex, and when in the compressed configuration, the first crossbar engages the second apex such that the first apex and the second apex move radially away from each other and the first anchoring member is moved radially inward further than the second apex.

2. The prosthesis of claim 1, wherein the first ring further comprises:
    a third apex;
    a first strut extending between the first apex and the third apex; and
    a second strut extending between the second apex and the third apex.

3. The prosthesis of claim 2, wherein the first crossbar extends toward the third apex.

4. The prosthesis of claim 3, wherein the second apex comprises a second anchoring member extending radially outward; and a second crossbar extending radially inward and away from the first apex.

5. The prosthesis of claim 1, wherein the first crossbar extends generally perpendicular from the first apex.

6. The prosthesis of claim 1, wherein the second apex does not comprise an anchoring member that extends radially outward.

7. The prosthesis of claim 1, wherein the first crossbar comprises a first portion that extends toward the second apex, and a second portion that extends away from the second apex.

8. The prosthesis of claim 1, wherein the first crossbar extends from the first anchoring member towards the second apex.

9. The prosthesis of claim 1, wherein the first crossbar is spaced a distance from the first anchoring member.

10. The prosthesis of claim 1, wherein the tubular frame comprises a cross support to couple the first ring to a second ring of the rings.

11. The prosthesis of claim 1, further comprising a graft coupled to the tubular frame.

12. A prosthesis delivery system comprising the prosthesis of claim 1; and a sheath, the first ring being disposed within the sheath and having the compressed configuration.

* * * * *